United States Patent
Westwood

[11] Patent Number: 5,810,795
[45] Date of Patent: Sep. 22, 1998

[54] HYPERBARIC DEVICE WITH SECONDARY PRESSURE ZONE

[76] Inventor: Joseph R. Westwood, 234 Polecat Rd., Glen Mills, Pa. 19342

[21] Appl. No.: 649,872

[22] Filed: May 13, 1996

[51] Int. Cl.$^6$ ..................................................... A61F 13/00
[52] U.S. Cl. .......................... 604/305; 604/23; 604/307; 128/202.12
[58] Field of Search .................... 604/304–307, 604/23; 128/202.12–202.13

[56] References Cited

U.S. PATENT DOCUMENTS

| | | | |
|---|---|---|---|
| 3,744,491 | 7/1973 | Fisher | 128/184 |
| 4,003,371 | 1/1977 | Fisher | 128/184 |
| 4,224,941 | 9/1980 | Stivala | 128/207.26 |
| 4,772,259 | 9/1988 | Frech | 604/23 |
| 4,911,699 | 3/1990 | Fenton | 604/333 |
| 5,029,579 | 7/1991 | Trammell | 128/205.26 |
| 5,154,697 | 10/1992 | Loori | 604/23 |
| 5,256,159 | 10/1993 | Newman | 604/317 |
| 5,411,496 | 5/1995 | Homa | 604/333 |
| 5,478,310 | 12/1995 | Cantwell et al. | 604/23 |
| 5,662,625 | 9/1997 | Westwood . | |

OTHER PUBLICATIONS

"A Simplified Hyberbaric Oxygen Technique for Leg Ulcers", Heng et al. Dermatology, vol. 120, May 1994, pp. 640–645.

Primary Examiner—Mark Bockelman
Attorney, Agent, or Firm—Robert J. Reichert

[57] ABSTRACT

A topical hyperbaric device comprising a gas treatment zone having a maximum pressure release valve that can be set at a desired treatment pressure and that is not connected to the gas supply, and a gas pressure zone adjacent to the treatment zone that applies pressure to the treatment zone to maintain the pressure in the treatment zone.

7 Claims, 2 Drawing Sheets

HYPERBARIC DEVICE WITH SECONDARY PRESSURE ZONE

BACKGROUND OF THE INVENTION

Many difficult to heal wounds, particularly where there is damage to the blood circulation system, are now treated with a gas such as oxygen to supplement the oxygen to the wound area that is not being satisfied by the damaged blood circulation system. Initially, this was done by installing a gas chamber around the wound and flowing oxygen continuously over the wound area. These chambers were rigid, heavy, difficult to clean between uses, and uncomfortable for the patient. Recently it has been discovered that continuous flow of oxygen is not necessary, and that effective hyperbaric treatment can be obtained by using a single adequate stationary charge of oxygen that is retained in a flexible chamber in contact with the wound for the treatment period. Unlike the continuous flow type devices, these devices do not need to be continuously attached to the oxygen supply during treatment, allowing mobility for the patient Many flexible topical hyperbaric bags are known. U.S. Pat. No. 5,154,697 assigned to Topox, Inc. discloses a hyperbaric bag that has a hole through the side of the bag that is to be exposed to the area to be treated. The periphery of the hole is reinforced with a strong ring. A belt structure affixes the bag over the area to be treated, and gas such as oxygen inflates the bag to the desired gas pressure. The device contains a gas inlet for charging, and a gas pressure release valve which is constructed for a fixed single maximum gas pressure. Unlike earlier hyperbaric devices, the device of this patent does not require a constant supply of gas. Although it is known that there are different narrow optimum pressures ranges for treating arterial wounds and venous wounds, the Topox bag is not designed to operate at a specific prescribed pressure. The devices cannot be ajusted to an optimum pressure in response to a wound diagnosis.

Dyson-Cantwell U.S. Pat. No. 5,478,310 discloses a large flexible hyperbaric oxygen bag used to enclose an entire leg for single gas charge treatment. It comprises a polyethylene bag to be secured around the leg and a gas supply line. This device does have a pressure control means but it is connected to the gas supply line. As shown in FIG. 3, the chamber may have a tape covering holes in the gas bag that can be pulled off the holes during treatment to decrease gas pressure. Using this device it is difficult, if at all possible, to set and maintain the treatment pressure within the range of desired treatment pressure.

The prior art also discloses numerous topical hyperbaric devices that apply a continuous supply of gas flowing through the wound area. These of course require continuous connection to the gas supply, eliminating patient mobility during treatment.

Some of these prior art continuous flow devices have pressure control valves that are connected to and control the gas input. See Stivala U.S. Pat. No. 4,224,921; Tramell U.S. Pat. No. 5,029,479; and Frech U.S. Pat. No. 4,772,259.

Pressure control means connected to the gas supply have several disadvantages. When the gas supply is disconnected or shut of, the pressure control means is disconnected or shut off, and so the pressure control means is no longer functional. This is particularly important for devices designed for static treatment use. Also, accurate control of the treatment zone pressure is difficult because such valves are not directly measuring the treatment zone pressure. Furthermore, putting a pressure control valve in the gas supply line requires using an additional device, in addition to the gas cylinder or hospital gas supply line. In such a device the gas supply line is not directly connected to the hyperbaric treatment device treatment zone.

Another serious shortcoming with current flexible hyperbaric devices, especially those used for static treatment, is that much more therapeutic gas is needed to inflate the treatment chamber and, more importantly, to maintain gas pressure in the treatment zone as gas leaks our of the device than is needed for optimum wound treatment. Many of the topical hyperbaric devices are designed for home use. Often the supply of therapeutic gas, such as oxygen, is limited and expensive. In use of such devices, most of the expensive therapeutic gas is used to inflate the treatment chamber and then to maintain it at the desired the treatment pressure, only a minor amount of which is necessary for the wound treatment. This is a particular problem with large devices such as the leg bag devices disclosed in Dyson-Cantwell et al. U.S. Pat. No. 5,478,310. A large cannister of gas is necessary to inflate such a device and maintain ifs treatment pressure, although only a small quantity of gas is needed for the treatment.

SUMMARY OF THE INVENTION

The topical hyperbaric devices of the present invention comprise a flexible substantially gas impermeable first sheet of material that is capable of confining the therapeutic gas to a restricted therapeutic gas treatment zone; means to affix said first sheet to make a restricted therapeutic gas treatment zone encompassing the wound, wherein the gas is kept in contact with the wound and is restricted from escaping from the treatment zone; means for introducing the therapeutic gas into the treatment zone; a pressure release valve capable of setting the maximum gas pressure of the treatment zone to the desired treatment pressure, which valve is in direct communication with the treatment zone but is not in direct communication with the means for introducing the gas, automatically releases gas from the treatment zone when the maximum pressure is exceeded, and can be pre-set at the desired maximum pressure in the zone; a flexible substantially gas impermeable second sheet of material capable of confining gas to a pressure zone adjacent to the treatment zone and applying pressure to the treatment zone; and means for introducing gas into the pressure zone.

Preferably the valve is manually adjustable so that the desired maximum pressure of the treatment zone can be set accurately to the appropriate pressured determined by diagnosis.

BRIEF DESCRIPTION OF THE DRAWING FIGURES

For a detailed description of the preferred embodiments of the topical hyperbaric device of the present invention, reference is made to the drawings in which.

DEFINITIONS

Figure 1:
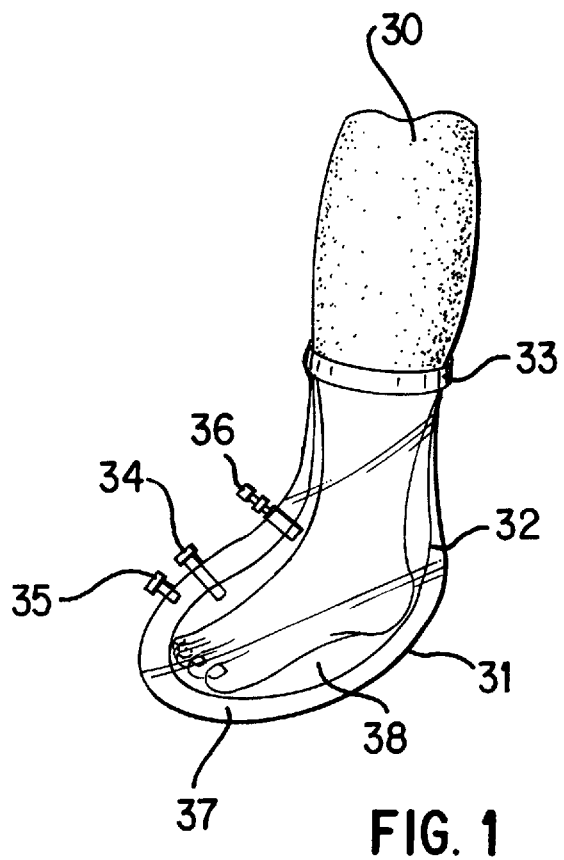
FIG. 1 is a prospective view of a preferred device of the present invention for treating a foot wound.

The term "maximum gas pressure" means the not-to-be exceeded highest gas pressure.

The term "optimum gas pressure" means the most effective therapeutic gas treatment pressure for achieving desired healing.

The term "pressure zone gas pressure" means the gas pressure in the pressure zone confined by the second sheet of flexible material.

The term "treatment zone pressure" means the gas pressure in the treatment zone confined by the first sheet of flexible material.

The term "desired maximum gas pressure" means the highest gas pressure in the treatment zone to be used in the particular treatment. It may be the exact pressure prescribed from the diagnosis, or it may be somewhat higher than the prescribed pressure to achieve an average of close to the prescribed pressure during treatment. In continuous flow treatment, the "desired maximum gas pressure" normally is the prescribed pressure.

The term "substantially maintain the gas pressure", as used herein in reference to the treatment zone gas pressure, means the gas pressure is maintained close to the desired maximum gas pressure by restricting escape of gas and/or adding gas during treatment. "Substantially" means to include deviation from the precise desired maximum gas pressure; this deviation may be as much as 30% or more so long as the deviation is not too much for adequate treatment in the particular case.

The term "retained", as used herein with respect to gas in the treatment zone, means the gas is kept in the treatment zone (static treatment, not continuous flow treatment). "Substantially retained" refers to the normal situation in static treatment wherein some gas leakage is expected, possibly requiring period replenishment.

The term "restricted", as used in reference to the treatment zone gas, means excessive uncontrolled escape of gas from the treatment zone is prevented. In static treatment, optimally "restricted" and "retained" mean completely prevented from escaping. Of course this level of restriction is seldom, if ever achieved, and so the term "restricted" is intended to include substantial gas escape so long as adequate therapeutic gas is maintained in the treatment zone. "Restricted" also applies to continuous flow treatment, where gas is continuously fed and exited from the treatment in a controlled manner while maintaining treatment zone pressure; uncontrolled escape of gas is minimized.

The term "substantially gas impermeable", as used herein with respect to the sheet material, means gas impermeable to the extend needed to prevent excessive gas escape from the treatment zone through the sheet material. Total gas impermeability seldom is needed, particularly for continuous flow treatment devices. However, generally high impermeability is desirable for static treatment devices.

The term "continuous flow treatment" means treatment during which gas is substantially continuously added and exited through most of the treatment period. It may include periods when the gas supply pressure is decreased, allowing treatment at a lower pressure, but the gas supply remains connected.

The term "static treatment" means treatment during which an initial charge of gas is retained in the treatment zone for a prolonged treatment time period, and there is no continuous flow of gas to the treatment zone during treatment. In static treatment, intermittent gas additions may be needed during the treatment period to replace escaped gas and maintain gas pressure.

DETAILED DESCRIPTION OF THE PREFERRED EMBODIMENTS

The present invention product is a flexible pressure controllable topical hyperbaric device for treating wounds and lesions with a therapeutic gas, particularly oxygen. The device comprises a flexible substantially gas impermeable first sheet of material capable of applying and confining a gas to the therapeutic treatment zone, which includes the area of the wound to be treated; means to deliver therapeutic gas the treatment zone; and at least one maximum pressure release valve means that is in direct communication with the treatment zone but is not in direct communication with the gas supply. The device also comprises a flexible substantially gas impermeable second sheet of material capable of confining gas to a pressure zone adjacent to the treatment zone and applying pressure to the treatment zone, and means for introducing gas into the pressure zone.

The pressure zone functions to maintain the pressure in the treatment zone, and also to minimize the required size of the treatment zone. Both of these functions minimize the amount of expensive therapeutic gas required.

Pressure in the treatment zone is maintained by the pressure zone because the common flexible wall between the to zones insures that both zones are at the same pressure when they are inflated. If the gas pressure in the pressure zone goes above the pressure in the treatment zone, the pressure in the pressure zone will in part be imparted to the treatment zone until both zones are at the same pressure. If this equalized pressure is above the pre-set pressure of the pressure release valve, the valve will release gas until the pressure in both zones is below the valve release pressure. In use, if therapeutic gas leaks out of the treatment zone and reduces the treatment zone pressure, the pressure zone/treatment zone common sheet flexible wall exerts pressure on the treatment zone until both zones are at the same pressure. The larger the size of the pressure zone in comparison with the treatment zone, the smaller the overall decrease in pressure caused by a leakage from the treatment zone. Elasticity of the pressure zone sheet material remote from the common wall can be used to increase this advantageous function of the pressure zone to maintain the pressure of the pressure zone.

Because of this gas pressure equalization effect and by taking advantage of a large relative size of the pressure zone and elasticity of the sheet material, present invention static devices are easily designed so that no supplemental therapeutic gas is needed after the initial charge. Furthermore, since air pressure gas may be supplied by a simple hand pump and a small portable oxygen cannister is sufficient for most devices, no unwieldy cylinder or other source of gas is needed.

The preferred pressure release valve means is a manually adjustable valve that can be set easily and accurately before use to whatever desired maximum gas pressure for the treatment zone is prescribed, insuring the correct pressure for the particular treatment. For example, when treating arterial wounds average treatment pressures in the range of 25–35 mm Hg above atmospheric are optimum, whereas when treating venial wounds pressures in the range of about 15–20 mm Hg. are optimum. A standardized hyperbaric treatment device of the present invention having a manually adjustable pressure release valve means can be used for whatever desired maximum pressure is prescribed. Desirably the valve means can be set accurately (either by an adjustable valve or by selecting the appropriate fixed pressure release valve element) accurately within the range of about 3 to 60 mm Hg., with an accuracy of about 10 mm Hg, preferably 5 mm Hg.

Referring to FIG. 1, a preferred device of the present invention is in the form of a foot bag. The lower part of a leg 30, having a wound for treatment thereon, is placed inside inner bag 32, which defines the hyperbaric treatment zone 38. Inner bag 32, the first sheet of material, is flexible, substantially gas impermeable, and capable of confining the therapeutic gas to treatment zone 38. Encompassing inner bag 32 is an outer bag 31, a second sheet of flexible substantially gas impermeable material capable of confining gas to pressure zone 37 Pressure zone 37 is adjacent to treatment zone 38 and when inflated applies pressure thereto. Bag 32 is a single common sheet of material between the treatment zone 38 and the pressure zone 37. Bags 31 and 32 are sealed together to make pressure zone 37 a gas-tight compartment. The top of the two bags 31 and 32 are jointly sealed tightly around the calf above the wound to make a substantially gas tight seal of the treatment zone 38 by tape 33, which may be an adhesive, snapping, tying or otherwise sealable tape. Gas inlet 35, which has a valve to prevent backflow of gas, is connected to gas pressure zone 37; gas inlet 34, which also has a valve to prevent bask flow of gas, is connected to treatment zone 38. Pressure release valve 34 is connected to treatment zone 38, and is in direct communication with the treatment zone but is not in direct communication with gas inlet 36. Valve 34 can be pre-set at the desired maximum gas pressure in the treatment zone and will automatically release gas from treatment zone 38 when the pre-set pressure is exceeded.

In use the foot to be treated is inserted into inner bag 32, and the device is securely sealed by tape 33. Gas line 34 is then connected to a means to supply the therapeutic gas to treatment zone 38 and turned on to inflate treatment zone 38 until pressure release valve 36 starts to release gas. Gas inlet 35 is then connected to a hand pump or other means to supply air to pressure zone 37 and the pressure zone 37 is inflated to the desired extent. Therapeutic gas treatment is continued for the prescribed period of time.

When static treatment is used, without continuous flow of therapeutic gas, gas inlets 34 and 35 are disconnected giving the patient mobility. If properly sealed, the device of FIG. 1 is capable of retaining a charge of therapeutic gas during an extended period of time. If the treatment zone leaks, it may be necessary to add pressure gas to outer bag 31 during treatment so that the desired therapeutic gas pressure in inner bag 32 is substantially maintained throughout the treatment period. When used for continuous flow treatment, a minimum amount of therapeutic gas is needed because the treatment zone in the present invention devices can be much smaller than the treatment zone of conventional hyperbaric treatment devices.

Figure 2:
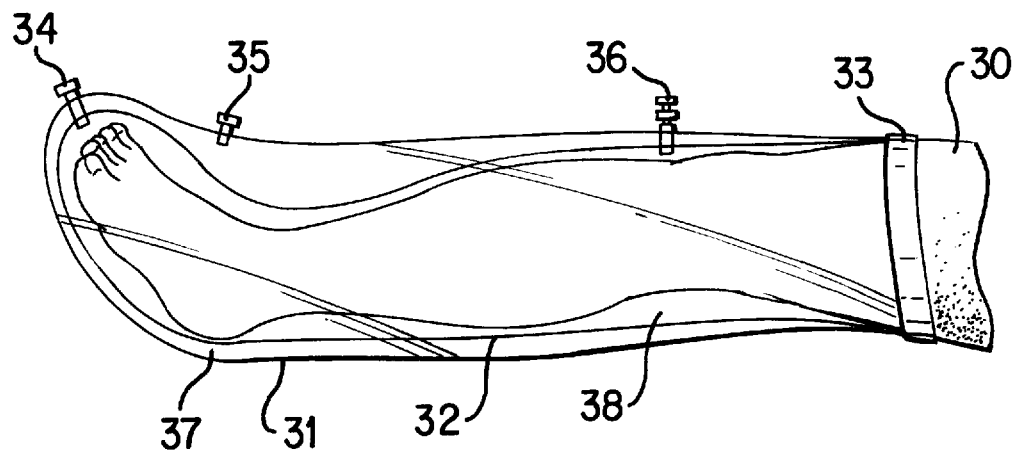
FIG. 2 is a prospective view of a preferred device of the present invention for treating a leg wound.

FIG. 2 shows a bag therapeutic device of the present invention similar to the device of FIG. 1, except that it is designed so that the entire leg can fit into the therapeutic treatment zone. The numbered parts in FIG. 2 correspond to their counterparts in FIG. 1. This type of device is excellent for either static or continuous flow treatment of a leg wound. This device is particularly useful for home care treatment, where the small amount of required therapeutic gas may be supplied by small cylinders. Only a minimum amount of therapeutic gas is required because, although the area of the patient being exposed is large, the treatment zone is small.

Figure 3:
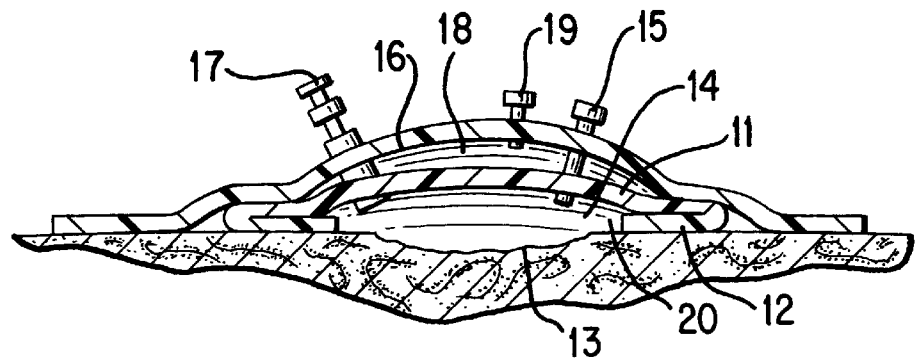
FIG. 3 is a cross section of a preferred device of the present invention for treating a body wound.

FIGS. 3.and 4 (not to scale) show the details of a preferred device of the present invention that is applied onto a body surface of a patient. This device is generally planar and comprises a first sheet 12 of flexible substantially gas impermeable material capable of confining gas to a therapeutic gas treatment zone. In this embodiment, sheet 12 is a double layer, the wound side layer having therein wound access opening 20, the periphery of which surrounds wound 13. The upper layer of sheet 12, securely sealed to the lower layer, along with the lower layer and the wound define treatment zone 14. This zone is relatively small in volume, compared to conventional hyperbaric devices for treatment of this type of wound. Affixed to the side of sheet 12 that is away from the wound is a second sheet 16 of flexible substantially gas impermeable material. Sheet 16 is bonded gas-tight to sheet 12 around the perimeter of sheet 12, whereby sheets 12 and 13 define a gas pressure zone 18. In the area where sheet 12 defines the pressure zone, sheet 12 is a single common sheet of material between the treatment zone 14 and the pressure zone 20. Both sheets 12 and 13 are capable of confining gas, and so pressure zone 18 is gas-tight. Therapeutic gas is fed to the treatment zone through gas inlet 15; pressure gas is fed to the pressure zone through gas inlet 19. Valve 17 is a pressure release valve capable of setting the maximum gas pressure in the treatment zone during the treatment Valve 17 is in direct communication with treatment zone 14 but is not in direct communication with gas inlet 15. Valve 17 can be pre-set at the desired maximum gas pressure in the treatment zone so that it automatically releases gas when the desired treatment pressure is exceeded.

Figure 4:
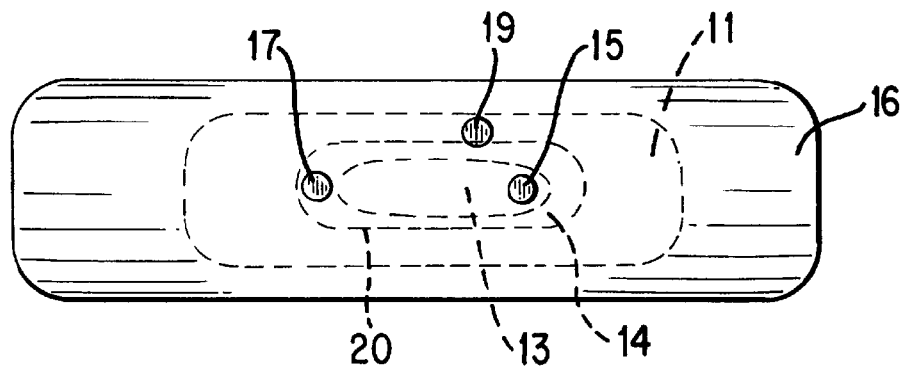
FIG. 4 is a top view of the device of FIG. 4.

In use, valve 17 of the device of FIGS. 3 and 4 is pre-set to the desired maximum pressure for the treatment zone, as determined by a wound diagnosis. The device is placed on the patient so that opening 20 surrounds the wound. The external surface areas of sheets 12 and 13 have thereon a layer of adhesive that prior to usage is covered by a release layer that is easily peeled off. The adhesive firmly affixes both sheets 12 and 13 to the skin of the patient out of contact with wound 13. Therapeutic gas is then fed into the treatment zone through gas inlet 15, which has a valve that prevents back flow of gas. Gas feed is continued until gas is discharged through valve 17. Pressure gas, normally air, is then introduced through gas inlet 19 into pressure zone 18 until the pressure zone 18 is inflated to the desired extent. In this device the pressure zone pressure functions to reinforce the sealing of treatment zone 20 to the patient. Like the devices of FIGS. 1 and 2, this device is ideally suited for use under static gas conditions where only a single charge of gas is needed, which is maintained at the desired treatment zone pressure by addition of pressure gas if needed. Of course if there is excessive leakage out of the treatment zone, supplemental therapeutic gas may be need. In any event only a minimum amount of therapeutic gas is needed when using this device because the pressure zone gas applies pressure to the treatment zone to maintain the pressure in the treatment zone. Also like the devices of FIGS. 1 and 2, this device can be used for continuous treatment, where the amount of therapeutic gas needed will be relatively small because of the pressure zone.

Devices similar to the devices of FIGS. 1 and 2, but not having a boot shape, can be used for hand and arm wounds. Also a single device without a boot shape can be used to treat both leg and arm wounds.

Figure 5:
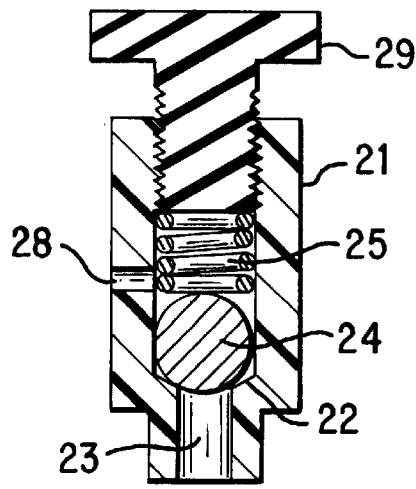
FIG. 5 is a schematic cross section of a manually adjustable pressure release valve suitable for use in the device of FIGS. 1 through 4.

FIG. 5 schematically shows a manually adjustable pressure release valve 17. This is a screw top valve that increases the treatment zone maximum pressure as screw 29 is screwed down. It comprises plastic cylindrical housing 21 that has an internal shoulder 22 at the bottom end with an opening 23 therein. Valve ball 24 seats on shoulder 22 sealing opening 23 closed. Tension spring 25 fits snugly above ball 24 along the inner sides of housing 21, and exerts the selected release pressure on ball 24. Spring 25 is designed to be able to exert about 5–60 mm Hg. on ball 25. Screw top 29 is threaded into the top of housing 21 so that it's plunger end abuts the top of spring 25. As screw 26 is screwed in it compresses spring 25, increasing the pressure on ball 24. When the pressure in the treatment zone exceeds the force of spring 25, ball 24 moves upward in the chamber of housing 21, allowing gas to escape from the treatment zone through opening 23 into the chamber of housing 21 and out through exhaust port 26.

Figure 6:
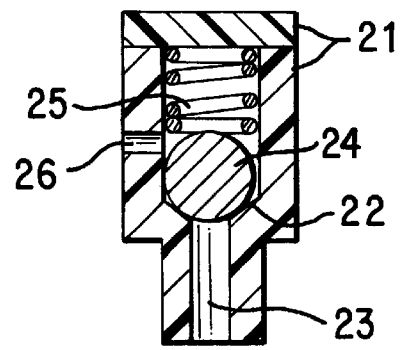
FIG. 6 is a schematic cross section of a valve having a readily replaceable fixed pressure release element, also suitable for use in the device of FIGS. 1 through 4.

Referring to FIG. 6, the pressure release valve need not be adjustable. Instead the valve may be a fixed release pressure female element that is easily inserted or screwed into a male receptacle in communication with the treatment zone. This device also comprises opening 23, ball 24, spring 25 and exhaust port 26, which function the same as there counterparts of FIG. 3. A selection of such fixed pressure release elements is made available, from which an element having the desired maximum release pressure setting is selected. These elements may be color coded to indicate their release pressure. When a fixed pressure release valve is used, the need for a pressure gauge is small.

The design of the pressure release valve is not critical. Many different types are suitable. For example, instead of a ball valve as shown in FIG. 3 and 4, the release valve can be a baffle valve such as a flap or butterfly baffle valve. Other valves are equally suitable, so long as they are capable of accurately setting the maximum release pressure and are inexpensive and so discardable. If desired the adjustable valve can be calibrated to show the pressure setting. The preferred valve bodies are made of any rigid plastic, although metals such as stainless steel can be used. The spring preferably is steel. Very inexpensive completely plastic valves can be used.

The pressure release valves of FIGS. 5 and 6 are inexpensive yet reliably accurate, within the preferred accuracy ranges. The entire hyperbaric treatment device, including the valve, is inexpensive and disposable. Using a valve that is in communication with the treatment zone and not with the gas supply eliminates the need for a separate pressure control mechanism between the hyperbaric treatment device and the oxygen source. The hyperbaric device can be connected directly to the gas cylinder or hospital gas supply line.

The material from which the two flexible sheets are made can be any strong substantially gas impermeable material. They can be the same or different material. Cast plastic sheeting material, such as polyurethane, polyethylene terephthalate, polyvinyl chloride, or ethylene/polyvinyl copolymer sheet stock, and vapor proof treated fabric such as nylon are suitable. Desirably the second sheet of material that confines the pressure zone has substantial elasticity because, as aforementioned, significant elasticity of the pressure zone sheet of material assists in maintaining the pressure in the treatment zone. For many uses it is desirable that the sheet materials be transparent. The flexible sheets can have a variety of shapes. Treatment zone sheet 12 is a rectangular two sided envelope configuration in FIGS. 5 and 6. It can be a single planar layer, or a bag to surround a limb. Also it can be a double layer cuff to go around a limb. For wounds on the back or buttocks, the rectangular planar envelope and single sheets are best suited.

The therapeutic gas to be used in the treatment zone normally is oxygen. Any prescribed therapeutic gas may be used in the present invention devices. The pressure gas normally will be air, which can be delivered from a hand pump. The type of pressure zone gas is not critical; it might be convenient to use oxygen, but air is far less expensive.

To treat a wound with a device of the resent invention, after the wound has been diagnosed to determine the desired maximum gas pressure for the treatment, an appropriate hyperbaric device of the present invention is selected. This device comprises a means not in direct communication with the gas supply to accurately set the maximum treatment zone gas pressure at the desired maximum pressure as determined by the diagnosis. This desired maximum pressure will be set to give an average treatment pressure, usually within the optimum ranges set forth above. The desired maximum pressure setting is achieved either by selecting a fixed release pressure valve that is fixed at the appropriate desired maximum pressure, or by using a hyperbaric treatment device having a manually adjustable maximum pressure valve and manually setting it at the desired maximum pressure.

The topical hyperbaric treatment device is then affixed to the patient to encompass the wound and make a treatment zone including the wound, into which gas is introduced and restricted from escaping. Sufficient therapeutic gas is then introduced into the treatment zone until the pressure release valve starts to release gas, indication that the gas pressure in the treatment zone is at the desired pre-set desired maximum pressure. Then pressure gas is introduced into the pressure zone until inflated to the desired extent. Thereafter, if leakage of therapeutic gas occurs inexpensive pressure gas is added until the pressure release valve in the treatment zone starts to release gas, thereby maintaining treatment gas pressure without adding expensive therapeutic gas.

Alternatively, the pressure zone may first be charged with gas to a predetermined pressure. If desired the pressure in the pressure zone can be controlled by an inlet gas pressure valve set slightly below the desired maximum pressure for the treatment zone. Or a pressure release valve like that connected to the treatment zone can be connected to the pressure zone to control the pressure in the pressure zone. Thereafter, gas is introduced into the treatment zone until the release valve starts to release gas.

The pressure zone applying pressure onto the treatment zone functions to help maintain the pressure in the treatment zone. Furthermore, in some device constructions such as in FIGS. 3 and 4, it also reinforces the sealing of the device to the wound area.

Whenever a static treatment gas device of the present invention is used, it will retain a single static gas charge of treatment gas for a prolonged period of time, the duration of which depends on how well the device is able to restrict the gas and retain it in the treatment zone. It may be necessary to add pressure gas to the pressure zone periodically to substantially maintain the desired maximum pressure in the treatment zone. When gas is added, addition is normally continued until the pressure release valve starts to release therapeutic gas, indication that the desired maximum pressure in the treatment zone has been reached. The need for additional gas can be noted by observing diminished volume in the treatment zone, i.e. a flattening bag. Alternatively the device may have a pressure gauge connected to the treatment zone. Since this static treatment device maintains the initial gas charge within the treatment zone substantially at the desired treatment level for a prolonged period of time, the device does not need to remain connected to either gas supply, giving the patient mobility. When pressure gas is needed this can be supplied by a simple hand pump. Further use of a source of therapeutic gas normally is not required for static treatment In using the device of the present invention, before treatment the wound is diagnosed to determine whether arterial or venous and the desired maximum treatment gas pressure, duration and sequence of treatments. Typically a 7 day treatment period is prescribed comprising identical one to two hour treatments on days 1, 2, 3 and 4, followed by no treatment on days 5 through 7, which treatment usually is repeated one or more times.

Although the invention herein has been described with references to particular embodiments, it is to be understood that the embodiments are merely illustrative of the principles and applications of the present invention. It is therefore to be understood that numerous modifications may be made to the embodiments and that other arrangements may be devised without departing from the spirit of the present invention as defined by the claims.

What is claimed:

1. A topical hyperbaric device comprising;
    (a) a flexible substantially gas impermeable first sheet of material capable of applying and confining gas to a therapeutic gas treatment zone;
    (b) means to affix said first sheet to make a restricted therapeutic gas treatment zone encompassing said wound, wherein the gas is in contact with said wound and is restrained from escaping;
    (c) means for introducing said gas into said zone;
    (d) a pressure release valve capable of setting the maximum gas pressure of said treatment zone during treatment of a patient which valve is in direct communication with said treatment zone but is not in direct communication with said means for introducing said gas, automatically releases gas from said treatment zone when maximum pressure is exceeded, and can be pre-set at the desired maximum gas pressure in said zone;
    (e) a flexible substantially gas impermeable second sheet of material capable of confining gas to a pressure zone adjacent to said treatment zone and applying pressure to said treatment zone; and
    (f) means for introducing gas into said pressure zone.

2. The device of claim 1 wherein said pressure release valve is fixed at a predetermined desired maximum treatment gas pressure.

3. The device of claim 1 wherein said pressure release valve is manually adjustable to the desired maximum treatment gas pressure.

4. The device of claim 1 wherein said means to affix is capable of retaining said gas in said treatment zone for a prolonged period of time.

5. The device of claim 1 wherein there is a single common sheet of material between said treatment and pressure zones.

6. The device of claim 1 wherein said second sheet of material has substantial elasticity.

7. The device of claim 1 wherein said means for introducing gas into said pressure zone is a hand pump.

* * * * *